United States Patent
Weber et al.

[11] Patent Number: 6,120,519
[45] Date of Patent: Sep. 19, 2000

[54] ADVANCED FULCRUM LIPOSUCTION DEVICE

[76] Inventors: Paul J. Weber, 1 Seneca Rd., Ft. Lauderdale, Fla. 33308; Michael R. Weber, 13906 Tern La., Clearwater, Fla. 33762

[21] Appl. No.: 09/203,413

[22] Filed: Dec. 2, 1998

[51] Int. Cl.⁷ .................................................. A61B 17/32
[52] U.S. Cl. ........................................... 606/170; 606/174
[58] Field of Search .................................. 606/169, 170, 606/171–175; 128/305

[56] References Cited

U.S. PATENT DOCUMENTS

| | | | |
|---|---|---|---|
| 4,815,462 | 3/1989 | Clark | 128/305 |
| 5,123,903 | 6/1992 | Quaid et al. | 604/22 |
| 5,353,798 | 10/1994 | Sieben | 128/772 |
| 5,514,091 | 5/1996 | Yoon | 606/192 |
| 5,601,582 | 2/1997 | Shetlon et al. | 606/170 |
| 5,665,101 | 9/1997 | Becker et al. | 606/170 |
| 5,755,753 | 5/1998 | Knowlton | 607/98 |
| 5,865,810 | 2/1999 | Perry et al. | 604/93 |

*Primary Examiner*—Michael Buiz
*Assistant Examiner*—Jonathan D. Goldberg
*Attorney, Agent, or Firm*—L. E. Carnahan

[57] ABSTRACT

A liposuction apparatus is provided which contains a shaft having a reinforced swan neck structure. The apparatus has a suction channel for removing fatty tissue and a channel for introducing cooling fluid material. Optionally, the tip of the shaft has a bezel for better separation of tissue and a sonic or ultrasonic generator.

28 Claims, 4 Drawing Sheets

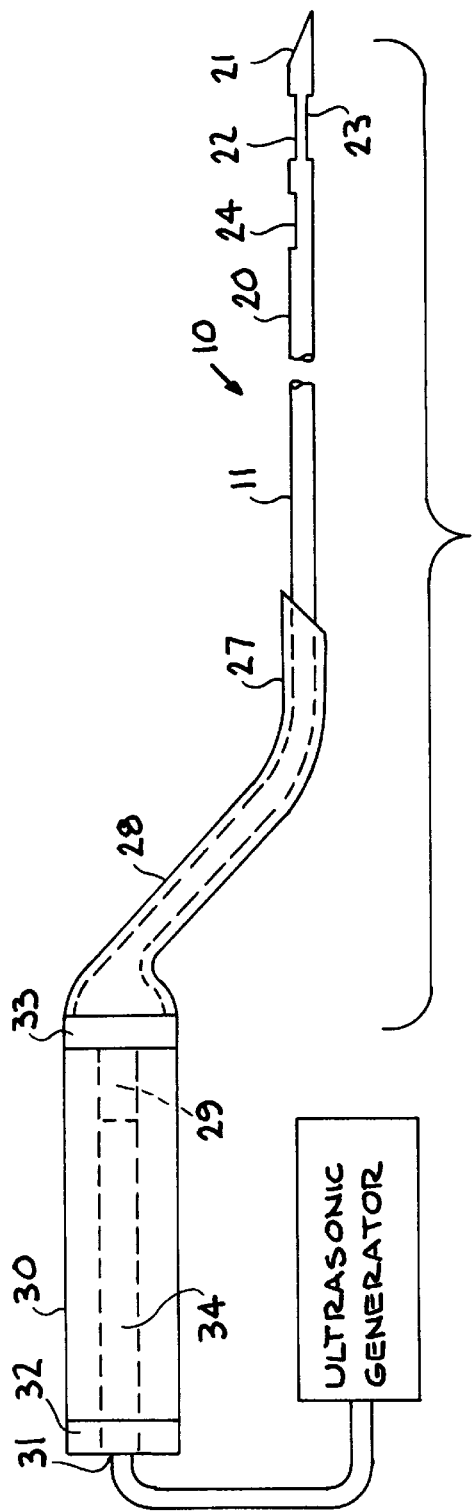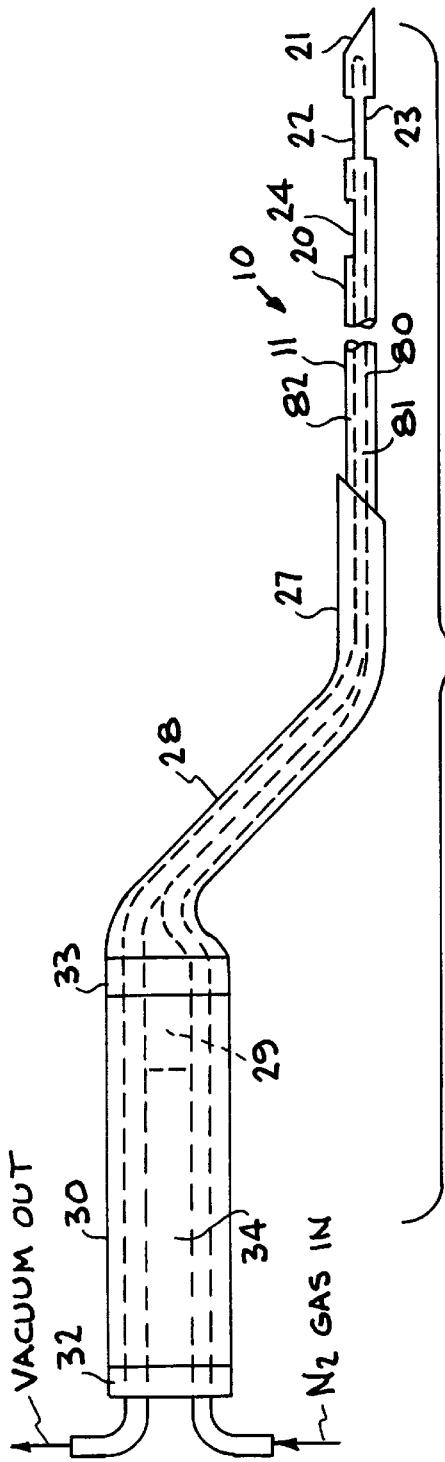

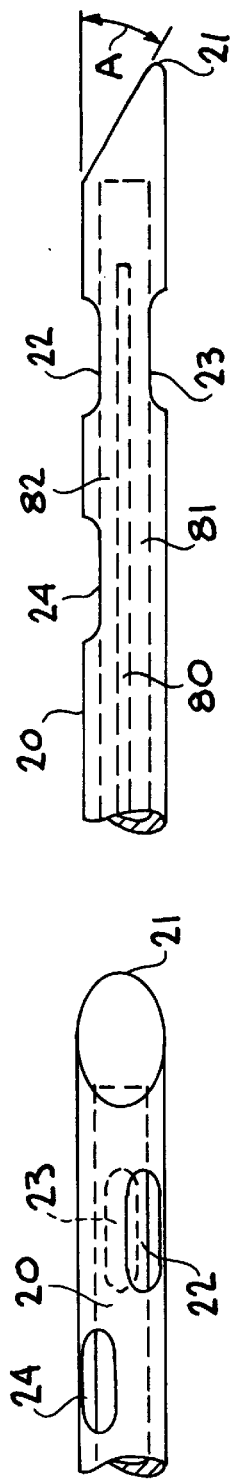
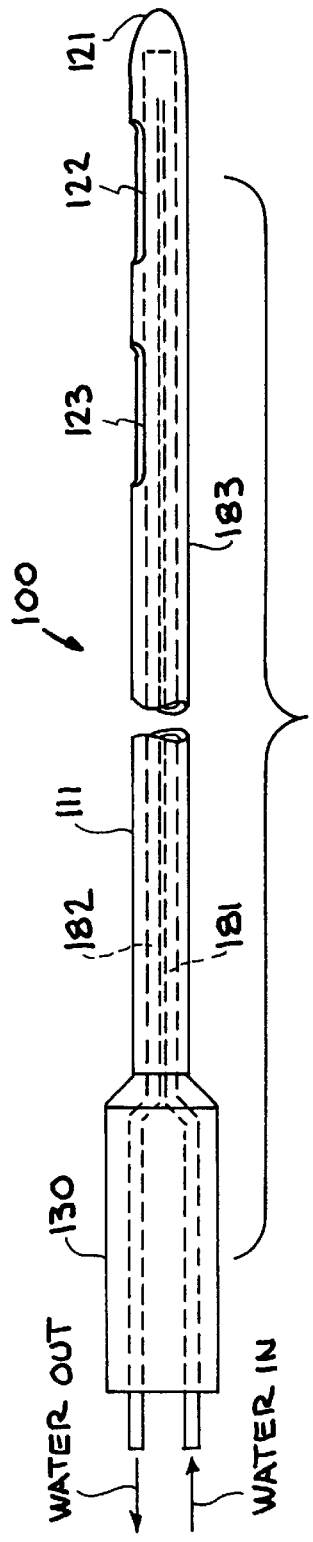
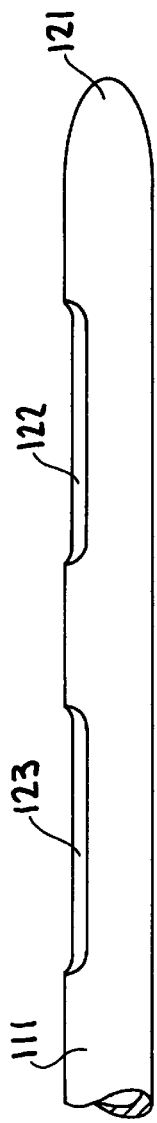

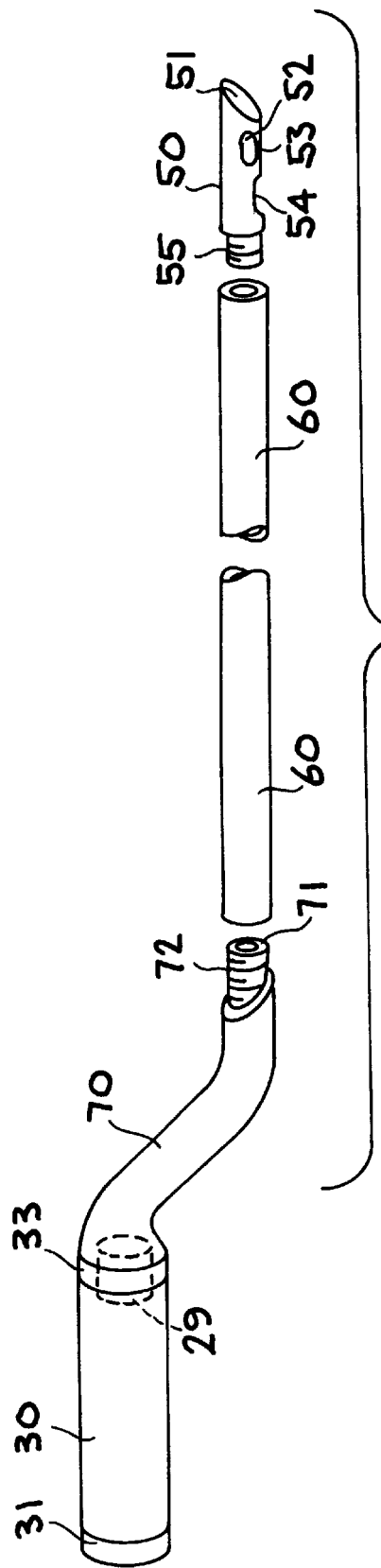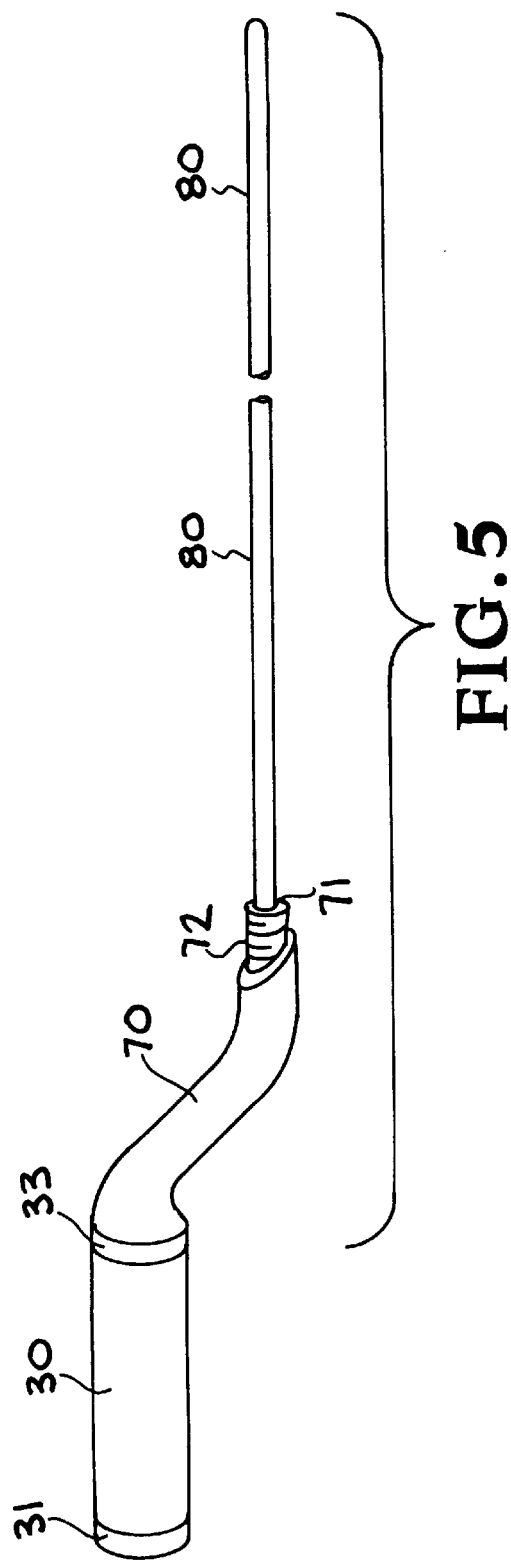

ADVANCED FULCRUM LIPOSUCTION DEVICE

BACKGROUND OF THE INVENTION

1. Field of the Invention

This invention relates to a liposuction apparatus and method. More particularly, this invention relates to a liposuction apparatus optionally having a sonic or ultrasonic source with an axial lumen passage, and is ideally suited for smooth continuous fat removal.

2. Description of the Prior Art

Liposuction, which literally means "fat suction", is a technique that pulls fat out of the body by means of teasing, pulling, scraping or suction. It can be used to reduce the volume of fat in many regions of the body, but is particularly effective in areas such as thighs and abdomen, which contain genetically determined fat not responsive to diet or exercise. Liposuction is currently an established modality in cosmetic surgery, performed by surgeons as an elective operation, and is one of the most common procedures in medicine.

All existing ultrasonic liposuction devices used in surgery, especially those with short rigid shafts, can cause complications and trauma by failing to have proper temperature control and improper placement in addition to increased entrance wounding.

A commonly accepted liposuction technique utilizes a cannula with a blunt closed bullet-shaped tip rather than an open tip or a pointed or sharpened tip. This cannula is a metal tube, about the size of a pencil, which is attached to a suction pump. The cannula, with its rounded tip, is sometimes passed through the fat first, without suction, to develop the proper passageway. Then suction is applied and the surgeon continues passing the cannula through the fat tunnels with repeated radial thrusts on several levels of the tissue. Adipose tissue is aspirated through a hole in the side of the cannula near its distal end. The cannula must be moved back and forth through each tunnel. Problems associated with this technique are similar to those experienced with the older methods of liposuction and include: oversuctioning, need for many entrance incisions, difficulty positioning patient, bleeding and resistance to passage in fibrous tissues.

Today there exists a wide variety of cannulas which allow surgeons to work more skillfully. For example, there is a bullet shaped tip, or curette-cannula where the suction holes have sharp edges. Rounded or bulbous shaped cannulas, such as bullet or basket-shaped tips, provide three dimensional forces on tissue at the tip which is concentric and conical. The disadvantage of these forces in penetrating highly fibrous fat tissue is that there is likelihood of increasing trauma to these areas vectoring particularly in highly fibrous fat tissue. This force vectoring has the consequence of increasing trauma to these areas. U.S. Pat. Nos. 4,886,491 and 5,514,086 to Parisi et al, both of which are incorporated by reference, describe cannulas having bullet or rounded tips.

A spatula cannula provides a two-dimensional force which allows for greater ease of movement with less exertion on the surgeon's part. The spatula concept has been incorporated into the design of the CAPISTRANO™ line of cannulas. The CAPISTRANO™ cannulas, marketed by Jeffrey Allan Klein, M.D., Inc., San Juan Capistrano, Calif., are more rounded and the bevel is oriented more along the center-line and in longer cannulas. Any increase in roundness or bluntness causes increased resistance to passage and thus affords less predictability and bending of an extending probe within patients.

It is also known to use ultrasonically vibrating and aspirating probes in the field of liposuction surgery, as described in U.S. Pat. No. 4,886,491 to the present inventors. The procedure is to introduce the vibrating probe into the area of material desired to be removed which has been preirrigated, and use the ultrasonic vibrations to physically breakup/loosen the fatty tissue. The fatty tissue can be emulsified by ultrasound and aspirated through the probe, using irrigation as an adjunct. It is known that a particularly effective probe for ultrasonic liposuction is a hollow cylindrical probe with a bullet shaped tip on the distal end. The tip can be welded or otherwise affixed to the probe. Both probe and tip can be manufactured from a variety of acoustically conductive metals such as cold-rolled steel, titanium, and aluminum. In presently known devices, the probe and tip are manufactured from the same materials, or from very similar materials, to ensure effective propagation of the ultrasonic waves all the way to the tip of the probe. Propagation of the waves to the distal tip of the probe is desirable, because this causes the tip of the probe to be able to loosen and emulsify fat, facilitating insertion of the probe into the fatty tissue.

In previously known liposuction techniques, before the use of ultrasound, considerable physical exertion was necessary to force the tip of the probe into the fatty tissue. This was time consuming and required more openings, and it required considerable strength on the part of the physician. The currently known ultrasonic liposuction probes are much more easily moved through the fatty tissue, because the top of the probe can loosen the tissue in advance of the probe. This essentially breaks a hole through the fatty tissue, rather than punching a hole by force.

There is a disadvantage sometimes associated with an ultrasonic probe having an acoustically conductive tip, however. For instance, when the probe has been inserted into the fatty tissue near the skin or the peritoneum, resistance can be met. When resistance is met, the wattage or temperature at the tip increases, and it can increase to the point of damaging the skin or the peritoneum or nerves. During such manipulations, the heat generated at the tip of the probe may be in excess of the ability of the tissues to safely dissipate the heat. In other words, if care is not exercised, the tip may be hot enough to burn tissues, damage muscles, blood vessels or nerves, and even penetrate membranes such as the skin or the peritoneum.

Another problem regarding the liposuction procedure involves the reduction or elimination of friction caused by the motion of the cannula by the surgeon. Applying lubricating jellies and the use of plastic stents are not satisfactory since the jellies must be constantly re-supplied and the plastic stents are difficult to maintain in position.

There remains a need in the art for new devices and methods for removing fatty tissue without damaging skin, nerves, or organs or forming ridges and other disadvantages resulting from conventional liposuction surgery. A need exists for devices and methods which would greatly assist those practicing liposuction to more efficiently remove unwanted fatty tissue, especially with reduced cannula entrance wounds.

SUMMARY OF THE INVENTION

In accordance with the present invention there is provided a liposuction device, a liposuction system and surgical methods of removing fatty tissue more efficiently. The liposuction device comprises:

a handpiece;

a longitudinal and highly flexible cannula having a novel reinforced swan neck and having a proximal section, a distal section and at least one axially extending channel, said channels being associated with a source for providing suction, the proximal end of the cannula being releasably attached to the handpiece; and a tip consisting of an opening positioned toward the proximate end two and adjacent openings which are located proximate to the distal end, and for a sonic or ultrasonic device, a source of sonic or ultrasonic energy.

Preferably, temperature sensors are utilized in the ultrasonic devices together with means for controlling tip temperatures.

A surgical incision anti-friction device comprising:

a funnel shaped structure having a generally cylindrical tapered outlet portion and a wide inlet portion, the tapered portion has a plurality of small projections around its circumference adapted to anchor said device in the incision.

In the liposuction method of the invention, the above defined liposuction device is inserted into the fatty tissue of a patient's body and the triport bezel tip is moved through the fatty tissue so as to tease and suck out the fatty tissue through the lumen towards the proximate end thereby removing the appropriate tissue from the body.

Advantageously, the reinforced swan neck uses the entrance wound opening as a fulcrum to redirect the probe tip and therefore to position the cannula.

One preferred embodiment of the present invention involves the use of a surgical incision anti-friction device in combination with the liposuction apparatus described above.

An object of the present invention is to provide an improved liposuction device, a surgical incision anti-friction device and an improved method for the removal of fatty tissues.

Another object of the present invention is to provide a procedure which minimizes injury to nerves and blood vessels and which minimizes overall trauma to tissues during a liposuction procedure while maximizing efficiency.

Another related object of the present invention is to provide such a device and method wherein blood loss and effort on the part of the surgeon are minimized.

A further object of the present invention is to provide a liposuction method which yields a more even reshaping of overlying skin surfaces than conventional procedures.

Still another object of the present invention is to provide such a liposuction device wherein the diameter of the lumen can be minimized especially for very thin patients or maximized for obese patients, the shaft component is flexible and has a recover memory, i.e. returns to original position, through a reasonable degree of bending.

Yet another object of the present invention is to provide a procedure wherein the number and the size of the skin incisions are minimized and are not further traumatized by the friction of the cannula shaft movement. Fat can be sucked via entrance wounds located at great relative distances from the target fat.

An associated object is to provide a method which allows a liposuction device to be accurately positioned thus more efficiently remove tissue. An additional benefit of said device is to reduce the need to reposition patients intraoperatively.

Additional objects of the present invention include the provision of a monitored and cooled sonic or ultrasonic liposuction probe which minimizes injury to nerves and blood vessels and which minimizes overall trauma to tissues during a liposuction procedure, relative to other liposuction procedures, which allows a more even reshaping of overlying skin surfaces than conventional procedures and/or which enables a surgeon to know where and how much fat is being removed.

A further object of the invention is to provide a liposuction device which does not leave ridges even on ultra thin patients.

A yet still further object is to provide an ultrasonic version liposuction device which can monitor and regulate by feedback the temperature at the tip.

These and other objects of the present invention will be apparent from the drawings and detailed descriptions herein.

BRIEF DESCRIPTION OF THE DRAWINGS

FIG. 1 is a side elevation longitudinal view of the improved non-ultrasonic version liposuction device including the handle connected to the flexible and hollow shaft having a high memory of recovery integrated with a reinforced swan neck shape and a triport tip having a bezel tip in accordance with this invention.

FIG. 2 is a longitudinal cut away side elevational view of the liposuction device shown in FIG. 1 showing a hollow cannula shaft with the novel triport tip having a bezel tip of the present invention.

FIG. 2A is a magnified top-view of the triport bezel edged tip body illustrated in FIGS. 1 and 2 which with an ultrasonic device contains a temperature sensor. FIG. 2B as a magnified side view of the tip of FIG. 2A.

FIG. 3 is a longitudinal cut away side elevational view of a liposuction device of the prior ultrasonic art.

FIG. 3A is a magnified close-up of the rounded tip of the prior non-ultrasonic art liposuction device of FIG. 3.

FIG. 4 is a longitudinal exploded view of a plastic containing liposuction device in accordance with this invention using threaded connections for the various components.

FIG. 5 is a longitudinal view of a metal guide shaft to be used in positioning the hollow of FIG. 4 when used in combination with a shaft of high flexibility and low memory.

DETAILED DESCRIPTION OF THE PREFERRED EMBODIMENTS

Figure 7:
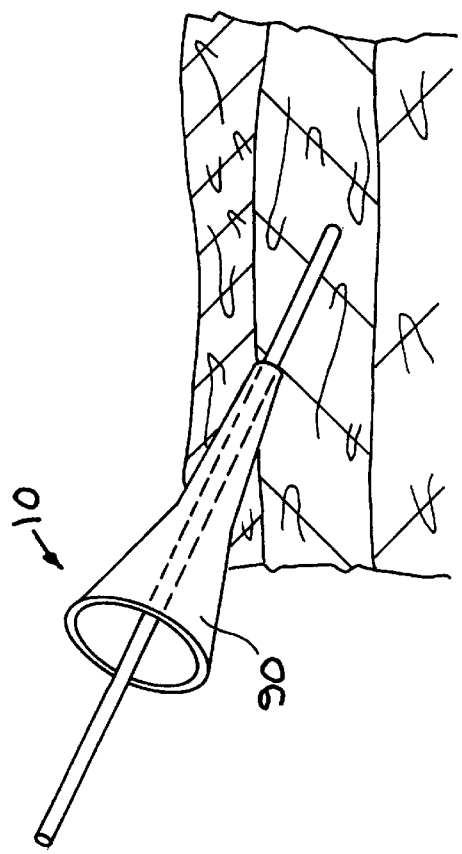
FIG. 7 illustrates the surgical incision anti-friction device for preferred use in combination with the liposuction device of the present invention.

In the embodiment shown in FIGS. 1, 2, 2A and 2B, the liposuction device 10 comprises: a handpiece 30 and an integrated cannula shaft 20 having a swan neck shape 28 at its proximal section and a triport tip 21 consisting of an opening positioned in the distal section proximate to two adjacent openings 23,24 which are located proximate to a bezel which forms the distal end. The hollow and flexible cannula shaft 20 is releasably connected to the front end 33 of handpiece 30 and longitudinally extends towards the distal end. In this embodiment, the cannula shaft 20 is shown integral with the triport tip portion 21. A stop assembly 33 couples the handpiece 30 with the cannula shaft 20. The rear part 31 of the handle 30 is operatively connected by stop assembly 32 to a suction means and optionally to a sonic or ultrasonic generating means (not shown) for aspirating fluid material through the handpiece channel 34 to channel 28 of the shaft 21 to the triport tip portion 20 at its distal end. Preferably, stop assembly 32 contains a microprocessor. However, the microprocessor can be located away from the handpiece. The triport tip portion 21 comprises a partially hollowed cylinder including an opening 22 positioned toward the proximal section and two adjacent openings 23 and 24 positioned toward a bezel which forms the distal end 22. In sonic and ultrasonic devices, the tip portion 21 and areas about the shaft contain a temperature sensor. The stop assemblies 32 and 33 can be integral with the handpiece 30. They are generally cylindrical and have a circular aperture with each end having inward facing threads. Preferably, the back portion of the handpiece is adapted for mounting of a supply conduit 31 for the suction means and sonic and ultrasonic waves to stop assembly 32. Preferably, the hand piece 30 is a QUICK-CONNECT™ handle marketed by KMI, Los Angeles, Calif.

For sonic and ultrasonic devices, there is a problem of overheating of the tip which may result in nerve damage. Therefore, it is preferable that the tip portion includes a temperature sensor such as a thermostat which is associated with a temperature control means which is separately associated with a device or housed in the handpiece 30. The temperature control means can comprise a microprocessor which is used to control the flow of cooling fluid to the tip. For example, if the tip reaches a selected temperature the amount of cooling fluid is increased. If the temperature is too low, the fluid is decreased. The preferred cooling fluid is nitrogen gas since only small diameter lumens are required to deliver the gas. After the cooling gas is delivered to the tip it is sucked back together with the fat through the shaft without escaping into the patient's tissue. The fat being removed which is cooled by the gas also cools the shaft when as it is sucked through the shaft length.

The cannula shaft 20 as shown in FIGS. 1, 2, 2A and 2B illustrates the reinforced swan neck shaped section 28 integrated with the longitudinal resilient portion including the triport tip portion 21 of shaft 20. The reinforced swan neck shape design allows for longer shaft lengths to be more easily controlled during the liposuction procedure at sites relatively distant from the entrance incisions. The swan neck portion 28 of the shaft is reinforced for several reasons. Reinforcement provides the needed stability to help a surgeon to increase leverage on the shaft 20 and to use as a guide in combination with the wound opening. The reinforcement may be consist of a flexible thickening material such as thermoplastic or thermoset polymers or a wire reinforcement or a metallic sleeve or jacket cannula. Preferably, the reinforcement comprises a thickening. The shaft is constructed of a material having excellent flexibility and memory characteristics. Metals and plastics are suitable materials of construction. Examples of plastic material include olefin polymers, fluorocarbon polymers and synthetic rubbers. Preferably polypropylene, polyethylene and tetrafluoroethylene and more preferably high density polyethylene are utilized. Examples of suitable metals include aluminum, cold rolled steel, stainless steel, titanium or a titanium alloy.

The outside diameter of the shaft ranges from about 2 millimeters to about 15 millimeters preferably less than about 10 millimeters. In particularly, preferred embodiments the cannula shaft 20 has an external diameter of 2 millimeters to about 8 millimeters, more preferably of about 3 millimeters, still more preferably of from about 2 millimeters to about 6 millimeters, and most preferably about 3 millimeters. The shaft is sufficiently rigid to permit repeated and controlled advancing strokes through the tissue.

The reinforced swan neck shaped portion allows for longer insertional lengths of the shaft which range from about 15 to about 35 cm and preferably from about 25 to about 33 cm.

The triport tip portion 21 has a single opening 25 positioned toward the proximal end, of the shaft 20 and two adjacent openings 23 and 24 are positioned toward a bezel which forms the distal end 22.

FIG. 2 shows schematically a cooling and aspiration system for use with the liposuction device of this invention. This system is formed within shaft 20 providing inlet channel 80 and outlet channel 82. The movement of the cooling and aspirating fluid material through inlet channel 80 is provided by a suction means (not shown) applied to the outlet channel 82. The excised tissue from the surgical site is aspirated via outlet channel 82 through hand piece 30 which rear end 31 is attached through a noncollapsible conduit to a collection means (not shown). Fatty tissue removal can be accomplished with a reduced need for a high negative pressure suction. The irrigating fluid may be saline, antiseptic, anesthetic solutions, hyaluronidase, heparin and epinephrine. The cooling fluid can be an inert gas such as nitrogen.

FIG. 2A illustrates a magnified close-up top view of the triport bezel tip portion 21. The bezel tip portion 22 comprises a cylindrical shape having a hollow proximal section and a solid distal section. The hollow proximal section has an opening longitudinally positioned toward the proximal end of the proximal section and two adjacent openings positioned proximate to a bezel which forms the distal end 22.

FIG. 2B shows a magnified close-up side view of the triport bezel tip portion 21 of the present invention. Angle A refers to the angle of inclination of the bezel to form the distal end or tip 21. Advantageously, angle A may be about 20 to 60 degrees and preferably about 35 degrees.

FIG. 3 shows a side view of a prior art ultrasonic cannula. A handpiece 130 is attached to a straight cannula 111. The distal tip of the straight cannula is of a thicker diameter than that of the present invention to capacitate channels 181 and 182 for the bi-direct flow of cooling fluid $N_2$ as well as aspirating channel 183. At the distal end, a basket or bulbous tip 121 with two openings 122 and 123 is shown.

FIG. 3A exhibits a magnified close-up side view of the rounded tip of the prior art non-ultrasonic liposuction device of FIG. 3. The deficiencies of this liposuction device have been discussed above.

In accordance with another variation of the present invention, plastic shaft and metal components of the liposuction device can be releasably attached to each other as shown in FIGS. 4 and 5. An exploded view of the liposuction device 40 shows the reinforced swan neck shaped portion 70 which may be threadedly engaged by male threaded portion 72 to cannula shaft 60 when the items are plastic. Likewise, at the distal end of the shaft 60, the triport bezel tip 50 is threadedly or permanently secured. Preferably, O-rings (not shown) are inserted between threaded connections to prevent fluid leakage. Alternatively, the releasable connections means may include snap fittings. FIG. 5 shows a flexible metal guide shaft 80 which is used in maintaining sufficient rigidity for positioning the liposuction device 40 within the surgical incision to the desired site of the fatty tissue to be teased and sucked out. The metal guide shaft 80 may be made from a metal material selected from aluminum, cold roll steel, stainless steel titanium or a titanium alloy.

The liposuction device according to the invention as illustrated in FIGS. 4 and 5 can be assembled quickly and easily prior to surgery and can fit within most sterilization apparatuses after use.

Figure 6:
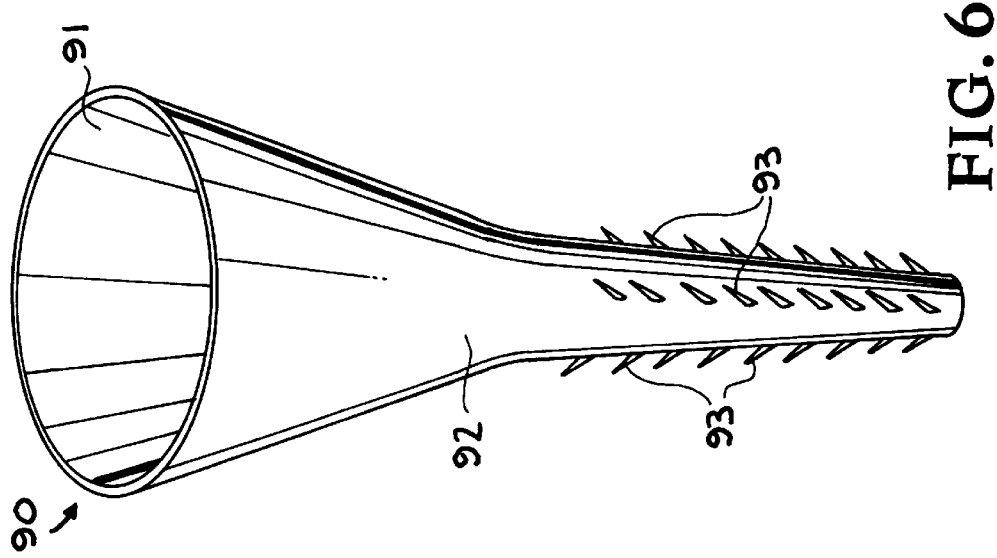
FIG. 6 illustrates an incision anti-friction device useful in combination with the liposuction device of the present invention.

FIG. 6 exhibits the novel callalilly-shaped surgical ultra-thin and flexible incision anti-friction device 90 of this invention which is useful in combination with the liposuction device described above.

The surgical incision anti-friction flexible device is funnel shaped having a wide portion 91 and a tapered portion 92 with a plurality of projections 93. The projections anchor the anti-friction device within the incision. The wide portion 91 can range from about 8 to about 16 millimeters and preferably about 12 millimeters. The narrow portion can range from about 2 to about 7 millimeters. Advantageously, the wide portion can be made of a thin flexible plastic material while the tapered portion should be semi-rigid. The projections are made of the same plastic material and range from about 1 to about 3 mm. The projections can be in the shape of hairs, pedals, ridges, and the like which provide a resistance to removal from the wound. Examples of suitable plastic materials include flexible thermoplastic polymers such as olefin polymers and fluorocarbon polymers. Specifically, high density polyethylene, high density polypropylene and polytetrafluoroethylene are preferred.

FIG. 7 illustrates a surgical callalilly-shaped incision antifriction device 90. This may be used in combination with the liposuction device 10, as shown in FIGS. 1, 2, 2A and 2B, in a preferred method of the present invention. A preferred method of the present invention provides for (a) the steps of forming an incision in the skin surface of a patient, (b) inserting the anti-friction device 90 through the incision, (c) inserting shaft 20 including the integrated triport bezel tip 21 through the anti-friction device 90 into subcutaneous fat tissues of the patient, (d) upon insertion of the triport bezel tip 21 through the incision, generating an optional ultrasonic pressure wave at the triport bezel tip 21, (e) transmitting the ultrasonic wave through the shaft 20 to establish a standing wave therein, (f) producing cavitation bubbles at the distal end of the triport bezel tip 21 in response to the ultrasonic standing wave, (g) liquefying fatty tissue of the patient, by virtue of the production of the cavitation bubbles, at a surgical site located at the distal end of the triport bezel tip 21, (h) applying suction in a fluid material through the channel 82 thereby aspirating the liquified fatty tissues through the appropriate channel, and (i) maintaining the distal end of the triport bezel tip 21 at approximately body temperature.

In the sonic and ultrasonic devices, the temperature sensor in the triport bezel tip 21 transmits the temperature to the handpiece 30. The microprocessor processes the information and controls the flow of cooling fluid, such as nitrogen gas to the bezel tip 21 so that the preselected temperature is maintained.

This method yields more consistent results than the prior art methods.

In a preferred ultrasound method, the cannula is vibrated at approximately 40,000 cycles per second at an amplitude of about 2 mil. This high frequency, low amplitude vibration serves to efficiently and safely separate the fatty tissue and create localized heat through frictional contact. Advantageously, this localized frictional heat serves to assist in the removal by physically melting a thin layer of surrounding fatty tissue.

Prior art sonic and ultrasonic apparatus useful with the liposuction device of the present invention include U.S. Pat. Nos. 3,526,219, 3,589,363, 4,223,676, 4,750,902, 4,886,491, 4,902,954 and 5,419,761 which are incorporated herein by reference.

In view of the consideration disclosed herein it is obvious that the modifications may be made to the invention such as having the procedure of assembling the various components, as well as, the sequence of inserting the device into the incision. For example, the cannula shaft may be initially inserted into the incision with or without the wire metal guide for the plastic model.

Thus, although the invention has been described in terms of particular embodiments and applications, one of ordinary skill in the art, in the light of this disclosure, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. In a liposuction device having;
   a handpiece;
   the improvement which comprises a longitudinal hollow and flexible cannula shaft having a proximal section and a distal section, said proximal section of said shaft comprising a reinforced swan neck shape which is capable of providing a fulcrum at the entrance incision wound of a patient and being connected to said handpiece said distal portion having a tip comprising at least one opening positioned toward the proximal end of the distal section; and
   a suction means operatively connected to said shaft at said proximal end for aspirating fluid material through said shaft.

2. The device of claim 1 including a temperature sensor in said cannula tip.

3. The device of claim 1 wherein including temperature control means associated with a temperature sensor whereby cooling fluid is controlled.

4. The device of claim 1 wherein a bezel forms the distal end.

5. The device of claim 1 having at least one channel for delivering fluid material to cool the cannula tip, shaft, and thereby the treated and affected bodily tissues.

6. The device of claim 1 wherein said device is ultrasonic and further contains at least one outlet channel having an outlet port for the introduction of the cooling fluid material to said tip and to fatty tissue and at least one suction channel for the evacuation of excised fatty tissue and spent cooling fluid.

7. The device of claim 6 wherein said cooling fluid material comprises inert gases or liquids.

8. The device of claim 1 which is further acoustically connected to sonic or ultrasonic means for imparting sonic or ultrasonic vibrations to said shaft or tip.

9. The device of claim 1 wherein said shaft is a metal.

10. The device of claim 1 wherein said shaft is a plastic material selected from an olefin polymer or a fluorocarbon polymer.

11. The device of claim 10 wherein said plastic material selected from high density polyethylene, high density polypropylene and polytetrafluoroethylene.

12. The device of claim 1 wherein said swan neck shaped portion of said shaft is reinforced with a thermoplastic polymer, a thermoset polymer, a fiberglass reinforced epoxy or a metal.

13. The device of claim 1 wherein said tip comprises a triport tip having a bezel with an angle that ranges from about 20 to about 60 degrees.

14. The device of claim 13 wherein the angle of the bezel on said triport tip is 35 degrees.

15. A liposuction device comprising:

a handle;

a hollow, flexible longitudinal shaft consisting of a proximal section and a distal section connected to said handle;

said shaft being composed of material selected from the group consisting of metal and plastic;

said proximal section having a reinforced swan neck shape which is capable of providing a fulcrum at the entrance incision sound of a patient; and said distal section having a multiport tip having configuration consisting of at least an opening positioned proximate to two adjacent openings which are located proximate to the distal end.

16. An ultrasonic liposuction device comprising:

a handpiece connectible to an ultrasonic source and a source for nitrogen gas and a source for suction;

means for controlling the flow of nitrogen and ultrasonic intensity;

a reinforced swan neck shaped conduit, a hollow flexible longitudinal metal cannula shaft and a triport tip, said swan neck is capable of providing a fulcrum at the entrance incision of a patient to redirect tip and to arc the path of the cannula;

said hollow flexible longitudinal metal shaft having a proximal section and a distal section and two channels, one of said channels delivering nitrogen gas from said source to said triport tip and to fatty tissue; the other of said channels being associated with said source of suction for removal of excised fatty tissue and spent nitrogen gas;

said swan neck shaped conduit connected at one end to said handpiece and at the other end to the proximal end of said proximal section of said shaft;

said triport tip having a temperature sensor associated with said temperature control means; and wherein said triport tip has a configuration consisting of an opening positioned proximate to two adjacent openings which are located proximate to a bezel which forms the distal end.

17. A surgical incision anti-friction device comprising:

a funnel shaped structure having a wide inlet portion and a tapered narrow outlet portion having a plurality of projections on the external surface, said projections are adapted to anchor said device into a surgical incision.

18. A method of liposuction comprising the steps of:

a) providing a longitudinal, hollow, and flexible shaft having a proximal end and a distal end, the proximal end being connected to a handpiece via a reinforced swan neck shaped member, the distal end being connected to a triport tip;

b) providing means for aspirating fluid material through the shaft;

c) forming an incision in the skin surface of a patient;

d) inserting an anti-friction means into said incision;

e) inserting the shaft through the anti-friction means and into subcutaneous fatty tissues of the patient hollow and flexible shaft having a proximal end and a distal end, said proximal end of said shaft having a reinforced swan neck shape and being connected to a handpiece and said distal end being connected to a multiport tip consisting of at least an opening proximate to adjacent openings which are located proximate to said tip and having a suction means operatively connected to said shaft at said proximal end for aspirating;

f) utilizing the incision as a fulcrum point for the shaft at the swan neck; and g) providing tip motion for teasing and removing tissue in the desired locations.

19. The method of claim 18 wherein said incision anti-friction means comprises a funnel shaped structure having projections for maintaining the anti-friction means in the incision.

20. The method of claim 18 further comprising imparting sonic or ultrasonic vibrations to said shaft tip for loosening the fatty tissue after step d) and further including the step of cooling said shaft tip and fatty tissue with nitrogen gas.

21. A liposuction device comprising:

a handle section, a highly flexible shaft section, and a reinforced swan neck section interconnecting said handle section and said flexible shaft section.

22. The liposuction device of claim 21, wherein said flexible shaft section includes a removable tip section.

23. The liposuction device of claim 22, wherein said tip section includes a plurality of spaced openings.

24. The liposuction device of claim 23, wherein said tip section additionally includes a bezel with an angle of about 20 to about 60 degrees.

25. The liposuction device of claim 21, wherein said flexible shaft is constructed of material selected from the group consisting of metal and plastic.

26. The liposuction device of claim 21, wherein said reinforced swan neck section is removably connected to at least said flexible shaft section.

27. The liposuction device of claim 21, wherein said flexible shaft section includes a reinforcement member mounted within said flexible shaft section.

28. The liposuction device of claim 21, additionally including means for equilibrating pressure to a distal end of said flexible shaft section and for removing fluid from said distal end.

* * * * *